United States Patent [19]

Ball et al.

[11] Patent Number: 5,976,165
[45] Date of Patent: Nov. 2, 1999

[54] ROTATIONAL ABLATION DEVICE HAVING REPLACEABLE SCREW-ON BURRS

[75] Inventors: Gregory Ball, deceased, late of Renton, by Patricia Ball, legal representative; Don Hogan, Snohomish, both of Wash.

[73] Assignee: SCIMED Life Systems, Inc., Maple Grove, Minn.

[21] Appl. No.: 08/988,127

[22] Filed: Dec. 10, 1997

[51] Int. Cl.⁶ .................................................. A61B 17/14
[52] U.S. Cl. .......................... 606/180; 606/159; 606/181; 606/170; 604/22; 604/24
[58] Field of Search .................. 606/180, 181, 606/182, 159, 170–173, 79–81; 604/22–24; 403/1, 7, 90

[56] References Cited

U.S. PATENT DOCUMENTS

| | | | |
|---|---|---|---|
| Re. 27,032 | 1/1971 | Hall | 606/180 |
| 4,747,406 | 5/1988 | Nash | 607/159 |
| 5,133,729 | 7/1992 | Sjostrom | 606/180 |
| 5,222,956 | 6/1993 | Waldron | 606/80 |
| 5,667,490 | 9/1997 | Keith et al. | |

FOREIGN PATENT DOCUMENTS 303810  2/1989  European Pat. Off. ................. 606/81

*Primary Examiner*—Michael Buiz
*Assistant Examiner*—Lien Ngo
*Attorney, Agent, or Firm*—Christensen O'Connor Johnson & Kindness PLLC

[57] ABSTRACT

The present invention provides for improved rotational ablation devices for use in medical applications designed to ablate a circular opening in a stenotic blood vessel wherein the rotational ablation device is provided with a replaceable cutting burr which allows the user to employ burrs of multiple sizes and configurations on a single rotational ablation device. The present invention also provides for a unique applicator tool which allows the user to readily remove and replace the novel cutting burrs of the present invention on a single rotational ablation device.

13 Claims, 3 Drawing Sheets

Fig. 2.A.

ROTATIONAL ABLATION DEVICE HAVING REPLACEABLE SCREW-ON BURRS

FIELD OF THE INVENTION

This invention relates to the field of rotational ablation devices which are capable of differentially cutting abnormal deposits from within a patient's blood vessels. More particularly, this invention is directed to an improvement which provides for the ability to replace the cutting burr on a rotational ablation device with one of a different size and/or configuration.

BACKGROUND OF THE INVENTION

Various prior art devices are known which allow a user to insert a catheter/guidewire means into a body cavity or blood vessel allowing the user to deliver an inflatable balloon, cutting device or other therapeutic means to a desired area. In carrying out such procedures, which may be generally described as either angioplasty or atherectomy, the objective is to open a stenotic segment of a blood vessel.

Angioplasty uses an inflatable dilatation balloon positioned in the artery to dilate the arterial lumen at the stenosis. A typical angioplasty device is disclosed in Bhate et al., U.S. Pat. No. 4,896,669. The angioplasty device of Bhate et al. includes an inflatable balloon which is attached to the distal end of a hollow catheter. The proximal end of the catheter is attached to a fluid source, providing fluid communication between the balloon and the fluid source.

To treat an arterial stenosis, the Bhate et al. balloon is introduced into the artery in a deflated state and guided through the artery over a guidewire to a position adjacent to the stenosis. Fluid from the fluid source is then infused into the balloon via the catheter to inflate the balloon. As the balloon expands, it dilates the lumen of the artery. The balloon is then deflated and removed from the artery.

While effective for dilating the lumen at the stenosis, angioplasty devices, such as the Bhate et al. device, do not remove plaque from the artery. Consequently, residual plaque either remains in place at the point of the stenosis or breaks off and migrates to other locations in the blood stream. In either case, the plaque remains a continuing threat to create blockages in the circulatory system. To address the shortcomings of angioplasty, a procedure termed atherectomy has been developed, whereby plaque comprising the stenosis is cut and removed from the blood vessel.

An atherectomy procedure typically includes inserting a guidewire into an affected artery and advancing a cutting device having a hollow shaft over the guidewire until the cutting device is positioned adjacent to the stenosis. The cutting device is then advanced into the stenosis to cut a channel through the plaque, thereby increasing blood flow through the artery. The resulting plaque fragments can be removed from the blood stream, for example, through the shaft of the cutting device, or if the fragments are sufficiently small, they can be removed from the blood stream by the body's reticuloendothelial system.

A number of atherectomy devices are known in the art. Farr et al., U.S. Pat. No. 4,895,166, discloses an atherectomy device having a frustum-shaped cutter which is attached to the distal end of a hollow catheter. The cutter has two openings that define two straight, even cutting blades. The cutter is directed through the artery over a guidewire, and it is rotated as it advances into the stenosis, thereby cutting the plaque. Excised plaque enters the openings of the cutter and is subsequently removed through the hollow catheter.

Auth, U.S. Pat. No. 4,990,134, describes a rotational ablation system which is itself an improvement upon the invention described in Auth, U.S. Pat. No. 4,445,509. The '134 patent teaches the use of an ellipsoidal abrading head, or burr, coated with tiny diamond chips (shovels). The abrading head rotates and causes differential cutting, whereby the abrading head differentiates between inelastic plaque, which is removed, and elastic arterial tissue, which remains undamaged. More specifically, it is taught that a tip (burr) of the type described, operating at a tip velocity of at least about 40 ft./sec., is able to abrade inelastic material at a high removal rate, while generating microscopic particles (on the order of 5 microns or less) and leaving behind a tissue base having a smooth appearance on the surface of the wall of the vessel from which an abnormal deposit has been removed.

Currently available rotational ablation devices such as those described in U.S. Pat. Nos. 4,445,509 and 4,990,134 employ a single cutting or abrading burr which is permanently attached to the rotating shaft of the rotational ablation device. Often burrs of different sizes are required during a procedure, and thus it is necessary to use an entirely new rotational ablation device each time the cardiologist desires to employ a burr of a different size. It has, therefore, been recognized that it would be advantageous to provide for a rotational ablation device which allows one to utilize different cutting or abrading burrs of varying sizes and configurations.

OBJECTS OF THE INVENTION

It is an object of the present invention to provide for improved rotational ablation devices for use in medical applications which allow for the use of abrading burrs of different sizes and configurations on the same rotational ablation device.

It is also an object of the present invention to provide for a threaded hub and abrading burr having a unique thread design which can be utilized in conjunction with the rotational ablation device of the present invention.

It is a further object of the present invention to provide for a novel applicator tool to be used in conjunction with the removal and insertion of the novel threaded burrs of the present invention.

These and other objects of the invention will become more apparent from the following discussion of the invention.

SUMMARY OF THE INVENTION

The present invention relates to an improved rotational ablation device wherein the rotational ablation device is provided with a replaceable burr. This allows the user to employ burrs of different sizes and configurations without having to discard the remainder of the rotational ablation system.

The present invention also relates to novel threaded hub and burr assemblies for utilization in connection with the rotational ablation device of the present invention.

The present invention further relates to a unique applicator tool which allows the user to readily remove and replace the novel burrs of the present invention on a single rotational ablation device.

The construction and obvious advantages of the present invention will best be understood from the following description of various specific embodiments when read in conjunction with the accompanying drawings.

BRIEF DESCRIPTION OF THE DRAWINGS

FIGS. 2 and 2a are partial cross-sectional schematic representations of the hub assembly of FIG. 1 and a replaceable cutting burr assembly showing the relative fit between the two;

DETAILED DESCRIPTION OF THE INVENTION

The devices of the present invention incorporate the use of a threaded cutting or abrading burr with stepped threads on a hub that creates an interference fit. Further, the present invention provides for an applicator and hub holding fixture, consisting of an integrated collet/clutch/removal fixture.

The thread mechanism employed in attaching the cutting or abrading burr of the present invention is unique because the hub threads have two distinct diameters. Initially a smaller diameter thread section allows the user to easily thread the burr for proper engagement with the hub assembly. The secondary thread section consists of two proximal threads, which are larger in diameter and engage a smooth proximal counterbore section in the cutting burr to create a locking interference fit.

The threaded cutting burr of the present invention features a smooth counterbore section that has the following functions:

1) The smooth counterbore section acts as a guide for the threaded hub to prevent cross threading; and
2) The smooth counterbore also interferes with the last, or proximal, two threads of the hub to create a locking interference fit as described above.

As discussed in greater detail below, the applicator/removal tool of the present invention has an applicator or collet assembly on one end to hold and apply a new burr to a driveshaft, and a removal assembly on the opposite end of the tool to hold and remove a used burr from a driveshaft. The collet assembly includes a selected collet configured to hold a selected burr in proper alignment to be attached to a driveshaft. Various collets may be used, configured to hold various sizes and symmetric or asymmetric burrs in proper alignment. The collet assembly includes a collet closure ring that when slid back, is locked in place. The collet assembly may therefore be used only once, thereby preventing the applicator end from being used again or as a removal tool. The removal assembly has a cavity to receive a used burr, the entrance to the cavity being surrounded by an E-ring assembly having a one-way locking push nut that captures the used burr in the housing of the tool and prevents the used burr from being reused.

The hub tool is designed around a 5" straight hemostat to provide a familiar and convenient tool for the user. It is also designed to hold the hub and drive shaft firmly, but still be atraumatic to the hub and drive shaft surfaces.

Figure 1:
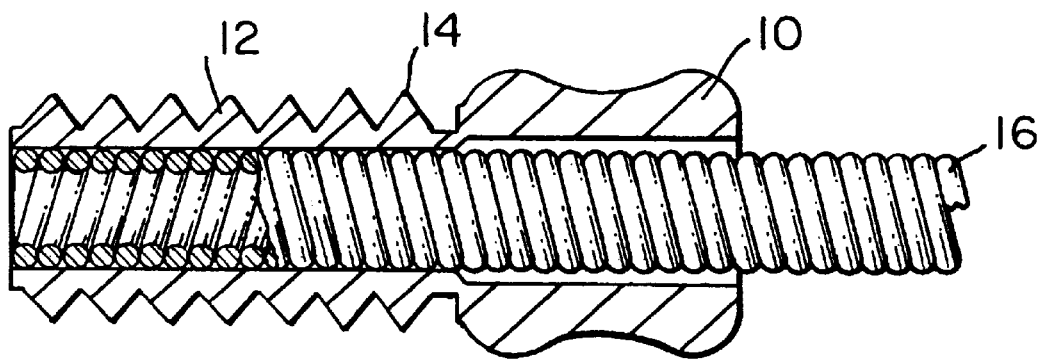
FIG. 1 is a schematic representation of a cross-section of a threaded hub assembly to be used in connection with the replaceable burrs of the present invention.

A preferred embodiment of the threaded hub assembly of the present invention is shown in FIG. 1. A hub assembly 10 has at one end a series of threads 12 of one exterior diameter, culminating in a series of two or more threads 14 having a slightly larger exterior diameter. The hub assembly is attached to the distal end of a rotating shaft 16, which shaft can be comprised of helically wound wires. See, for example, the flexible drive shafts described in U.S. Pat. Nos. 4,445,509 and 4,990,134, incorporated herein by reference.

Figure 2:
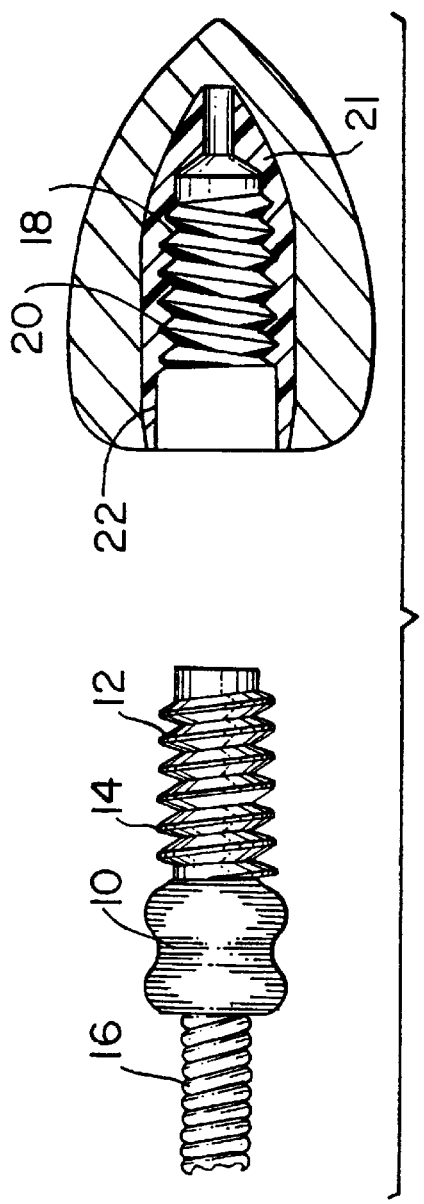
Figure 2:
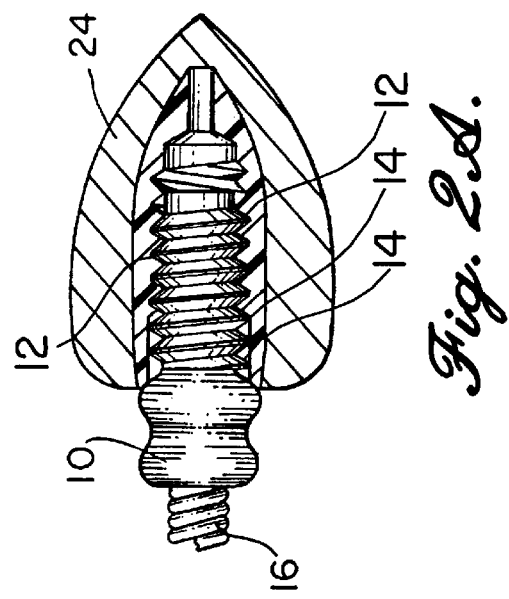

FIG. 2 depicts in partial cross-section the hub assembly 10 of FIG. 1 with its varying diameter screw threads 12 and 14 attached to rotating shaft 16 and its inter-relationship with the interior element 18 of a replaceable cutting or abrading burr 24. Burr 24 has inner member 21 which has mating screw threads 20, which correspond to the smaller screw threads 12 on the hub assembly 10. The inner member 21 of burr 24 is also provided with a smooth proximal counterbore section 22 that engages larger screw threads 14 to create an interference fit. Burr 24 with hub assembly 10 inserted is shown in FIG. 2a.

Figure 3:
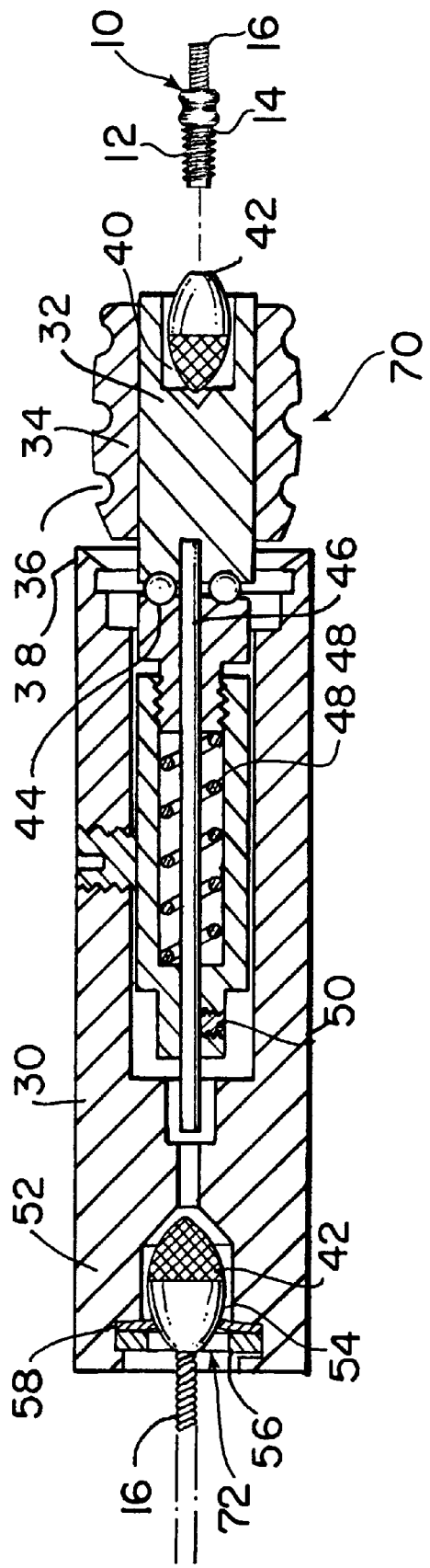
FIG. 3 is a schematic representation of a cross-section of a unique applicator/removal tool of the present invention showing its various components and its interaction with a replaceable cutting burr of the present invention.

A cross-sectional view of the applicator/removal tool of the present invention is shown in FIG. 3. The applicator/removal tool comprises housing section 30, having an applicator or collet assembly 70 on one end that is press-fit over shaft 46, and a removal assembly 72 on the opposite end of the tool. The collet assembly 70 holds and applies a new burr 42 to a driveshaft while the removal assembly 72 receives and captures a used burr that is removed from a driveshaft.

The collet assembly 70 has a collet 32, collet closure ring 34, and a collet ring lock 36, which engages a mating lip 38 on the collet end of the applicator/removal tool housing 30 when collet closure ring 34 is pushed toward the housing to release the burr 42. The collet 32 is provided with an opening 40 which can be of varying dimensions and configurations to engage and hold various cutting burrs 42 in proper alignment to be attached to a driveshaft. The collet 32 holding the burr 42 allows for the smooth attachment of the burr 42 to a hub assembly 10 by rotating the collet to screw the end of the burr onto a mating threaded end of the hub assembly 10. As discussed previously, the hub assembly 10 is bonded to a rotating shaft 16.

The applicator/removal tool housing is provided with a ball detent clutch assembly 44 which is designed to matingly engage the end of the collet assembly and matingly engage a spring housing assembly 48. The spring housing assembly is provided with a set screw 50 in order to lock the spring housing/collet assembly in position about the shaft 46.

A selected burr 42 is provided in the tool, held captive in the collet 32. The collet holds the burr 42 firmly because the collet closure ring 34 is pushed firmly over the collet (to the right in FIG. 3, as shown). The collet is rotated as a threaded hub assembly 10 coupled to driveshaft 16 is gently pushed into the burr until the burr is firmly threaded onto the hub, with threads 12 and 14 fully engaged, as illustrated in FIG. 2a. When the burr is firmly threaded onto the shaft 16 via hub assembly 10, the ball detent clutch 44, which is spring-activated by spring 48, begins to slip, thereby preventing the burr from being over-tightened. The burr is then released from the tool by pushing the collet closure ring 34 off the collet 32 towards the tool (to the left in FIG. 3). The collet ring lock 36 of closure ring 34 snaps into engagement with mating lip 38 as the burr is released. The engagement of the collet ring lock and lip 38 retains the collet closure ring so the tool cannot be reused. Also, because the collet closure ring is retained by the housing, the collet cannot be used to remove a burr non-destructively, thereby preventing the burr from being reused.

The proximal end 52 of the applicator/removal tool housing is provided with a removal assembly 72 having an opening 54 which is designed to accommodate or receive a used burr 42 when one wishes to remove the burr 42 from the hub assembly 10. The opening 54 is also provided with an E-ring assembly 56 and a one-way locking push nut 58 that the burr 42 pushes through as it enters opening 54. The opening 54 and locking push nut 58 capture and retain the used burr 42 in the housing, thereby preventing the used burr from being removed from the housing and reused.

Figure 4:
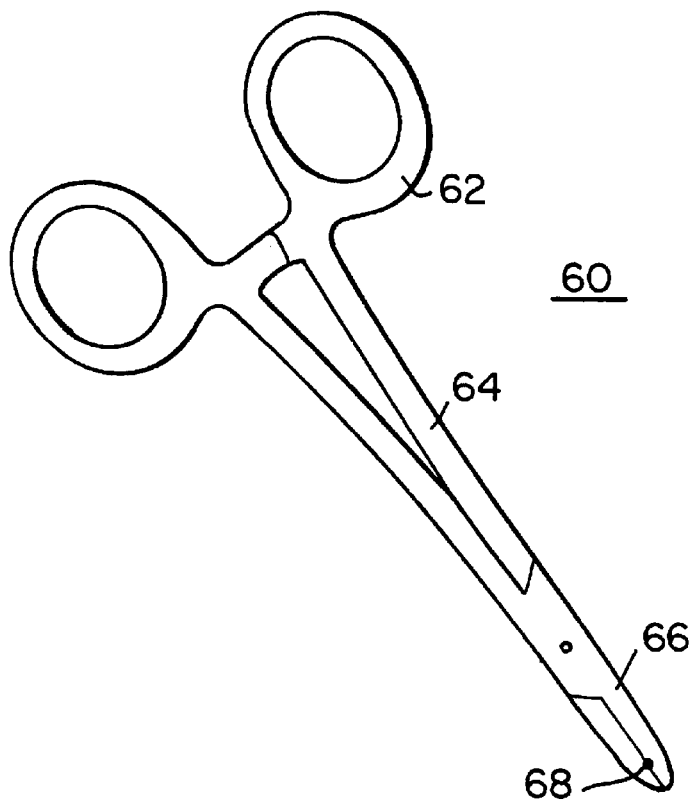
FIG. 4 is a schematic representation of a hub gripping tool.

In FIG. 4 a hub gripping forceps 60 is a variation of standard scissors or forcep devices. Finger grips 62 are connected through members 64 to gripping blades 66. Blades 66 each have a recess 68 that enables blades 66 to grip a hub of a burr according to the invention. The forceps 60 can be made from stainless steel or any other suitable material.

It will be generally understood by one skilled in this art that the materials of construction of the hub, and interior elements of the burr assembly may be of any suitable material. Preferably the hub 10 will be fabricated from stainless steel or brass. The interior elements of the burr assembly will preferably be fabricated out of brass or any suitable polymeric material, such as DELRIN®.

Generally speaking, the applicator/removal tool housing will be constructed out of aluminum or any other suitable light weight material which is not subject to corrosion or deterioration when exposed to normal body fluids.

The overall length of the hub assembly 10 will be from about 0.10 to 0.40 in., preferably from about 0.12 to 0.20 in., and will have a maximum outside diameter of from about 0.03 to 0.10 in., preferably from about 0.04 to 0.08 in. The diameter of threads 12 and 14 is from about 0.02 to 0.08 in., preferably from about 0.035 to 0.07 in., with threads 12 being slightly smaller than threads 14. However, these dimensions are not critical and may be altered as would be apparent to one skilled in this art. The important consideration insofar as the hub assembly is concerned lies in the provision for a threaded section which has a section of proximal threads which are of larger diameter than the initial section of threads on the hub assembly.

As would be apparent to one skilled in this art the interior dimensions of the internal elements of the cutting burr assembly will be such as to properly mate with and interact with the hub assembly provided.

The critical feature with regard to the cutting burr assembly is the provision for a counterbore section which interferes with the proximal oversized threads provided on the hub assembly to create the required locking interference fit.

The specific dimensions of the various elements of the applicator/removal tool assembly are not critical so long as the various components which are designed to interact with the cutting burr assembly and to grasp the hub assembly on the rotating shaft are properly sized and aligned to accomplish their intended purpose as would be apparent to one skilled in this art.

It will be further apparent to one skilled in this art that the improvements provided for in the present invention, while described with relation to certain specific physical embodiments also lend themselves to being applied in other physical arrangements not specifically provided for herein, which are nonetheless within the spirit and scope of the invention taught here.

It is claimed:

1. In a rotational ablation device for use in medical applications to ablate an opening in a stenotic blood vessel, the improvement wherein the rotational ablation device is provided with a rotatable driveshaft and a replaceable burr which allows the user to employ cutting burrs of multiple dimensions and configurations on a single rotational ablation device, wherein the distal end of the driveshaft comprises a hub assembly with exterior threads and the replaceable burr has interior screw threads, wherein the exterior threads of the hub assembly comprise a first section of threads having a first exterior diameter and a second section of threads having a second exterior diameter that is larger than the first exterior diameter.

2. The rotational ablation device of claim 1, wherein the first exterior diameter of the first section of threads is from about 0.02 to 0.08 in.

3. The rotational ablation device of claim 2, wherein the hub assembly is larger in exterior diameter than the threads and has an overall length of from about 0.10 to 0.40 in.

4. The rotational ablation device of claim 1, wherein the hub assembly is fabricated out of stainless steel or brass.

5. The rotational ablation device of claim 1, wherein a threaded cutting burr has been matingly attached to the hub assembly, said burr having interior screw threads to matingly engage the first section of threads on the hub assembly and which burr has a smooth interior proximal counterbore section to engage and interfere with the proximal section of threads on said hub assembly.

6. A hub assembly for use in attachment to a rotating driveshaft in a rotational ablation device comprising a threaded end having a section of threads of one exterior diameter and a proximal section of threads having a larger exterior diameter.

7. The hub assembly of claim 6 which is fabricated of stainless steel or brass.

8. A cutting burr assembly comprising a cutting burr having an exterior cutting surface and an interior section of threads to matingly engage a first section of threads on a hub assembly, which cutting burr is also provided with a smooth interior proximal counterbore section to matingly engage a second section of threads on the hub assembly, the second section of threads having a larger exterior diameter than the first section of threads.

9. The cutting burr assembly of claim 8, wherein the interior thread and counterbore sections are fabricated of brass or a suitable polymeric material.

10. An applicator/removal tool to apply and remove a cutting burr to/from a hub assembly attached to the end of a rotatable shaft comprising:

a housing having a first collet end;

a collet assembly having a collet closure ring and a collet ring lock to engage a mating lip on the collet end of the housing, said collet assembly also being provided with a first opening to engage and hold a cutting burr in proper alignment to allow smooth attachment of the cutting burr to a threaded end of a hub assembly; and a second end of said housing distal to the first collet end being provided with a second opening to receive and hold the cutting burr for removal of the cutting burr from the hub assembly, said second opening being provided with an E-ring assembly and a one-way locking push nut through which the cutting burr passes as it is placed in the second opening, the E-ring assembly and one-way locking push nut retaining the cutting burr in the housing while the cutting burr is removed from the hub assembly.

11. A tool for applying and removing a cutting burr from a rotatable driveshaft comprising:

a housing provided with a first end and a second end distal to the first end;

a collet assembly coupled to the first end of the housing, the collet assembly having a collet provided with a first recess to receive and hold a cutting burr while the cutting burr is coupled to a driveshaft; and a second recess provided in the second end of the housing to receive and hold a used cutting burr while the used cutting burr is uncoupled from a driveshaft, a retention member being aligned with the second recess to capture the used cutting burr in the housing.

12. The tool according to claim 11 wherein the collet assembly has a collet closure ring that is moveable from a first position substantially surrounding the collet to a second position captured by the housing, the collet assembly releasing the cutting burr when the collet closure ring is moved to the second position.

13. The tool according to claim 11 wherein the cutting burr is threaded onto a threaded end of the driveshaft by rotating the collet, the collet being coupled to a clutch assembly that prevents the cutting burr from being over tightened onto the driveshaft.

* * * * *